United States Patent [19]

Elbaum

[11] Patent Number: 4,880,836

[45] Date of Patent: Nov. 14, 1989

[54] ANTIVIRAL AMPHIPHILICS

[76] Inventor: Danek Elbaum, Box 450, Awosting Rd., Pine Bush, N.Y. 12566

[21] Appl. No.: 166,890

[22] Filed: Mar. 11, 1988

[51] Int. Cl.$^4$ ............................................. A61R 31/17
[52] U.S. Cl. .................................................... 514/588
[58] Field of Search ......................................... 514/588

[56] References Cited

U.S. PATENT DOCUMENTS 4,223,041  9/1980  Pigerol et al. ...................... 514/588

Primary Examiner—Jerome D. Goldberg
Attorney, Agent, or Firm—Lackenbach Seigel Marzullo & Aronson

[57] ABSTRACT

The present invention relates to contacting HIV virus, or the host cells, with a lower-alkyl-urea to prevent viral penetration into the cells, thus preventing viral infection.

15 Claims, No Drawings

ANTIVIRAL AMPHIPHILICS

BACKGROUND OF THE INVENTION

1. Field of the Invention

The present invention relates to contacting HIV virus, or their host cells, with a lower-alkyl-urea to prevent viral penetration into the cells, thus preventing viral infection.

2. The Prior Art

Studies into the nonviral medical effects of alkylureas are known.

(1) "Effect of Alkylureas on the Polymerization of Hemoglobin S", by Danek Elbaum et. al., Reprinted from the Proceedings of *The National Academy of Sciences*, Vol. 71 No. 12, pp. 4718–4722, December, 1974.

(2) "Dissociation of Human Hemoglobin by the Ureas and Amides Osmotic Pressure and Light Scattering Studies", by Danek Elbaum et. al., Reprinted from *Biochemistry*, (1974) 13, 1268, Copyright 1974 by the American Chemical Society.

(3) "Denaturation of Human and Glycera dibranchiata Hemoglobins by the Urea and Amide Classes of Denaturants", by Danek Elbaum, et. al., Reprinted from *Biochemistry*, (1974) 13, 1278, Copyright 1974 by the American Chemical Society.

(4) "Molecular and Cellular Effeots of Antisiokling Concentrations of Alkylureas", by Danek Elbaum et. al., *Blood*, Vol. 48, No. 2 (August), 1976.

(5) "The Inhibitory Effect of Alkylureas and Alkylamides on the Gelation of Hemoglobins", by Theodore T. Herskovits and Danek Elbaum, Biochimica et Biophysica Acta, 622 (1980) 36–51 Elsevier/North-Holland Biomedical Press.

A study was made of the antiviral activities of certain derivatives of N-phenyl-N'-(aryl or alkyl) thiourea against poliovirus. This was reported in the literature article, "Inhibitory Effect of N-Phenyl-N'-Aryl or Alkylthiourea Derivatives on Poliovirus Multiplication in Cell Cultures", by A. Galabov et. al., *Chemotherapy*, 17:161–174 (1972).

A study was made of the antiviral aotivities of certain derivatives of N-phenyl-N'-(aryl or alkyl) thiourea against coxsackie virus. This was reported in the literature article, "Antiviral Activity of N-Phenyl-N-'Aryl- or Alkylthiourea Derivatives in Coxsackie Virus Infections in Mice", by Angel S. Galabov et. al., *Antimicrobial Aqents and Chemotherapy*, Jan. 1974, pp. 1–8.

U.S. Pat. No. 3,872,171, 4,087,552, 4,258,061, and 4,491,583, (Cronin et. al.), relate to the use of various amines and amides, including urea derivatives, to combat infection by the encephalomyocarditis virus. However, all of the urea derivatives are disubstituted and may have substituents which include alkyl. At least one alkyl must have twelve or more carbon atoms. Each reference teaches that for there to be antiviral activity, that the urea nitrogen cannot have hydrogen or lower alkylsubstituents only, but that there must be at least one alkyl of twelve or more carbon atoms.

SUMMARY OF THE INVENTION

It is an object of this invention to provide a composition for preventing infection by the HIV virus, eg., HIV-1 or HIV-2 or by the hepatitis virus (Hepatitis A or Hepatitis B).

It is another object of this invention to provide a viral infection preventing or combating composition comprising an nontoxic pharmaceutical carrier and an effective antiviral amount of a monosubstituted lower-alkyl urea.

The present invention relates to the use of lower-alkyl-ureas which are monosubstituted, to prevent or to combat infection caused by any living viruses, such as the HIV virus, or the hepatitis virus.

Other viruses containing hydrophobic residues on the cellular membrane are believed to be inhibited or rendered ineffective as a result of a hydrophobic nature of the alkylureas, eg., picornavirus, reovirus, myxovirus, paramyxovirus, rhabdovirus, caronovirus, papovirus, adenovirus, herpesvirus, poxvirus and human hepatitis.

The present invention is directed to a method for preventing or combating infection in host cells caused by a live virus, and preferably by the hepatitis virus or HIV virus, comprising contacting either said virus or said cells with an effective antiviral amount of a monosubstituted lower alkyl urea, as the active ingredient.

The present invention is further directed to a method for preventing or combating infection in host cells of a warm-blooded animal caused by a live virus, and preferably caused by the HIV virus, or the hepatitis virus, comprising administering to said animal an effective antiviral amount of a monosubstituted lower-alkyl-urea, as the active ingredient.

DETAILED DESCRIPTION OF PREFERRED EMBODIMENTS

The acquired immunodefiency syndrom (AIDS) has been recognized as a disease since 1981 (M. Gottlieb et. al., *New Eng. J. Med.*, 305,1425, 1981). It has been postulated by Lane and Fauci (*Annu. Rev. Immunol.*, 3,477, 1985) that the infection results depletion and abnormality of T cells expressing a surface glycoprotein known as CD 4 antigen. Dalgleish et. al., in 1984 observed that the CD4 antigen is an essential component of the receptor for the AIDS retrovirus (Dalgleish et. al., *Nature*, 312,763). This was demonstrated by the ability of the antibody to CD4 to inhibit syncytia formation. Even more direct evidence, on the macromolecular level, has been presented by Smith et. al., (Science, 238,1704, 1987) who by a direct binding test demonstrated the role of the high affinity CD4–gp120 binding site. It is reasonable to postulate, on the basis of the available data, that infection by the virus requires the presence of an active binding site on the surface of the viral membrane which binds to a receptor on the host cell surface. This implies that by alteration of the binding site one can inhibit the infection. Two modes of binding site manipulation have been proposed: a) by AL 721 (the mechanism has not been defined, however extraction of the membrane cholesterol was suggested); b) by blocking of HIV-1 infectivity by a soluble form of the CD4 antigen.

A novel approach according to the present invention is that of blocking the HIV-host binding sites by alkylureas due to their hydrophobic binding to the glycoprotein comprising the active site of the virus attachment.

Alkylureas is a family of chemicals with the ability to inhibit HIV infectivity in direct proportion to their relative hydrophobicity for the lower alkyls of 1 to 8 carbon atoms. Up to 77% of inhibition of HIV infectivity has been observed by the syncytia test in the presence of butylurea (Table 1). The reported finding is that the degree of the effectiveness against infectivity is related to the length of the alkyl residue. This is the first clear demonstration that the mechanism of HIV infectivity is hydrophobic in its nature.

Contrary to the prior art teachings discussed above, it has now been unexpectedly found that monosubstituted lower-alkyl-ureas of the formula I:

$$R-NH-CO-HN_2 \qquad \qquad I$$

wherein R is lower alkyl, or alkyl having from 1 to 8 carbon atoms, desirably alkyl having from 1 to 6 carbons, preferably alkyl having from 1 to 4 carbon atoms, and most preferably alkyl having from 3 to 4 carbon atoms. Specific examples of R include methyl, ethyl, propyl, isopropyl, butyl, isobutyl, tertiary butyl, pentyl, hexyl, heptyl and octyl which enable the alkylurea to be useful as antiviral agents in the prevention and/or cure of infections caused by HIV virus, or caused by the hepatitis virus.

The monosubstituted lower alkyl ureas of formula I are known compounds, and can be prepared by methods known to those skilled in the art.

While not being bound by any particular theory for the operability of the monosubstituted lower-alkyl-urea as being effective against viral infections, it is believed that these ureas may have surface active, or surfactant, properties. The alkyl-urea compounds are comprised by a combination of nonpolar and polar moieties (amphiphilic character). The nonpolar moiety refers to the lower alkyl group which is believed to alter, or to interfere with, the ability of the virus to penetrate into the cell through the cell membrane. The polar moiety refers to the urea group which promotes water solubility for the antiviral agent.

In general, alkylureas are considered to be class II additives (as suggested by Brandts, J.F., in "Structure and Stability of Biological Macromolecules", p. 259, Marcel Dekker, Inc., 1969 ed. by Timasheff, S.N. and Fasman, G.D.) having hydrogen bonding properties.

It is believed that the mechanism by which a virus attacks a host, or target, cell is by membrane to membrane interaction which is a hydrophobic interaction, involving nonpolar moieties. A virus which is to attack the host, or target cell, would first approach the cell and would attach itself to the cell at a receptor binding site along the outside of cell membrane. The virus would then be able to penetrate through the cell membrane into the host cell, and to absorb the target cell into the virus.

It is believed that by contacting either the virus, or the target cell, or both, with an effective antiviral amount of the alkylurea surfactant, that the alkylurea prevents viral penetration into the target cell. The alkylurea antiviral agent is believed possibly to block the virus by coating the virus or by binding to its membrane with the hydrophobic nonpolar moiety, such that the polar or hydrophobic moiety of the host cell is rendered inactive.

Also, the alkylurea antiviral agent is believed possibly to block the virus by binding or coating the target cell at the binding receptor site of the cell with the hydrophobic or polar moiety of the alkylurea such that the polar or hydrophobic moiety of the alkylurea at the receptor site prevents the hydrophobic or polar virus from adhering to and attaching to the receptor binding site of the cell.

In other words, the alkylurea may coat either the virus, or the target cell, or both, and thus interfere with viral penetration into the cell.

However, the possibility that alkylureas interfere with viral infection by binding to intracellular material cannot be excluded due to their known high membrane permeability.

In order to protect the target cell, the virus is contacted with an effective antiviral amount of the alkyl urea antiviral agent, such as in vitro, for example on surfaces whereon the live virus may be located. The antiviral agent may be topically applied in a nontoxic pharmaceutical carrier, such as an aqueous solution in distilled water, or as a solution in a nontoxic polar organic solvent or as a suspension or an emulsion in a nontoxic cream composition.

Examples of suitable nontoxic polar organic solvents include lower alkanols of 2 to 6 carbon atoms, such as ethanol, lower alkanediols of 3 to 6 carbon atoms such as propylene glycol, lower alkanetriols of 3 to 6 carbon atoms, such as glycerol, and alkanehexols such as sorbitol.

Examples of suitable nontoxic cream compositions include a suspension or an emulsion of the active ingredient in a nontoxic nonhydrophobic cream, for example, a silicone emulsion or a polyethylene glycol emulsion.

When applying the antiviral surfactant of the present invention in a disinfectant composition to a vegetable, mineral or man-made surface, or when applying it topically to a warmblooded animal in a composition, the composition will contain an effective antiviral amount of the active ingredient which is from about 0.5 by weight up to about 90% by weight based upon the total weight of the composition. Desirably an effective amount of the active ingredient is from 1% by weight up to 50% by weight based upon the total weight of the composition, and preferably an effective amount of the active ingredient is from 2.5% by weight up to 20% by weight based upon the total weight of the composition.

When the antiviral surfactant is to be administered as the active ingredient to a warm blooded animal, an effective antiviral amount is from 0.5 mg/kg body weight to 10 g/kg body weight, desirably from 1 mg/kg body weight to 100 mg/kg body weight, and preferably from 5 mg/kg body weight to 50 mg/kg body weight.

Warm-blooded animals include mammals, such as mice, rats, guinea pigs, dogs, cats, monkeys and humans.

Several methods of administration are useful, for example, orally, intravenously or by injection, by absorption, by adsorption, extracorporealy, for example, by preincubation of blood or its components or other cells or tissue followed by readministration to warm-blooded animals. An example of extracorporeal application is in blood banking or other tissue banking. Topically the composition may be applied externally as a dry powder, liquid solution, or cream emulsion to the affected area of the body of the warm-blooded animal. Topically it may also be applied in a suitable transdermal patch such as the applicator described and claimed in U.S. Pat. No. 4,557,723. Oral administration includes tablets, capsules or in a syrup prepared by known methods. Intravenous, or injection, administration includes a solution in sterile distilled water prepared by known methods.

The present invention will now be described by reference to the following examples which are not to be deemed limitative of the present invention in any manner thereof.

EXAMPLE 1

H-9 cells were preincubated with various concentrations of alkylureas. These cells are highly permissive to HIV viruses. In culture, H-9 cells can tolerate concentrations of up to 150-200 millimolar of alkylurea. The cells were then washed and incubated with live HIV, which were not weakened in any manner. To quantitate the extent of HIV infection of H-9 cells, the alkylurea-H-9 cells preincubated with HIV were washed, and then incubated with CEM-SS cells that form Syncytia, (i.e., clumps of fused cells), if infected by HIV.

Three petri dishes A, B and C of H-9 cells were tested with alkylureas at 100 millimolar. Two petri dishes D and E of H-9 cells were tested with alkylureas at 1:2 dilution in distilled water producing 50 mM alkylurea.

Syncytia were quantitated by light microscopy. At 100 millimolar of alkylureas, test results indicated that the suppression of HIV infection (decrease in syncytia numbers), increased with the length of the urea side chain. Namely, butyl urea manifested the highest suppression, relative to the methyl urea which had a lesser suppressive power.

In Example 1, petri dish A was employed and the number of Syncytia formations was 25 for 100 mM methyl urea.

In the control samples, there were no live HIV virus, and hence there were no "Syncytia" formations seen under the microscope.

EXAMPLE 2

Utilizing a procedure analogous to that described in Example 1, except that petri dish B was employed, there were found to be 22 Syncytia formations for 100 mM methyl urea.

EXAMPLE 3

Utilizing a procedure analogous to that described in Example 1, except that petri dish C was employed, there were found to be 23 Syncytia formations.

EXAMPLE 4

Utilizing a procedure analogous to that described in Example 1, except that petri dish D was employed and there was a 1:2 dilution of the cellular suspension exposed to methyl urea, there were found to be 14 Syncytia formations.

EXAMPLE 5

Utilizing a procedure analogous to that described in Example 4, except that the petri dish E was employed, there were formed to be 8 Syncytia.

EXAMPLE 6

Utilizing a procedure analogous to that described in Example 1, except that ethyl urea was employed in the amount of 100 mM, there were found to be 23 Syncytia in petri dish A.

EXAMPLE 7

Utilizing a procedure analogous to that described in Example 6, except that petri dish B was employed, there were found to be 25 Syncytia.

EXAMPLE 8

Utilizing a procedure analogous to that described in Example 6, except that petri dish C was employed, there were found to be 19 Syncytia.

EXAMPLE 9

Utilizing a procedure analogous to that described in Example 6, except that petri dish D was employed and there was 1:2 dilution of the cellular suspension exposed to ethyl urea, there were found to be 14 Syncytia.

EXAMPLE 10

Utilizing a procedure analogous to that described in Example 9, except that petri dish E was employed, there were found to be 10 Syncytia.

EXAMPLE 11

Utilizing a procedure analogous to that described in Example 1, except that propyl urea was employed in the amount of 100 mM, there were found to be 14 Syncytia using petri dish A.

EXAMPLE 12

Utilizing a procedure analogous to that described in Example 11, except that petri dish B was employed, there were found to be 16 Syncytia.

EXAMPLE 13

Utilizing a procedure analogous to that described in Example 11, except that petri dish C was employed, there were found to be 12 Syncytia.

EXAMPLE 14

Utilizing a procedure analogous to that described in Example 11, except that petri dish D was employed and there was 1:2 dilution of the cellular suspension exposed to propyl urea, there were found to be 9 Syncytia.

EXAMPLE 15

Utilizing a procedure analogous to that described in Example 14, except that petri dish E was employed, there were found to be 10 Syncytia.

EXAMPLE 16

Utilizing a procedure analogous to that described in Example 1, except that butyl urea was employed in the amount of 100 mM, there were found to be 4 Syncytia, using petri dish A.

EXAMPLE 17

Utilizing a procedure analogous to that described in Example 16, except that petri dish B was employed, there were found to be 7 Syncytia.

EXAMPLE 18

Utilizing a procedure analogous to that described in Example 16, except that petri dish C was employed, there were found to be 5 Syncytia.

EXAMPLE 19

Utilizing a procedure analogous to that described in Example 16 except that petri dish D was employed and there was a 1:2 dilution of the cellular suspension when exposed to butyl urea, there were found to be 2 Syncytia.

EXAMPLE 20

Utilizing a procedure analogous to that described in Example 19, except that petri dish E was employed, there were found to be 2 Syncytia.

The results from all of these examples indicate that the monosubstituted lower alkyl ureas have the following advantages. They are very effective active ingredients in antiviral compositions to prevent and to combat infections cause by HIV viruses. The suppression of the HIV infection increased with the length of the alkyl side chain on the urea. These antiviral active ingredients may be utilized to treat surfaces of all kinds, to treat warm-blooded animals, and to treat blood supplies in a blood bank or hospital or a tissue bank.

The test results are summarized in the following table. The tests were conducted at room temperature.

TABLE

| HOST CELLS | | ALKYL UREA | CONTROL VIRUS | PETRI DISH SYNCYTIA OBSERVED A | B | C | D | E |
|---|---|---|---|---|---|---|---|---|
| CEM-SS | + | Methyl Urea | No Virus | 0 | 0 | 0 | 0 | 0 |
| | | | + HIV | 25 | 22 | 23 | 14 | 8 |
| CEM-SS | + | Ethyl Urea | No Virus | 0 | 0 | 0 | 0 | 0 |
| | | | + HIV | 23 | 25 | 19 | 14 | 10 |
| CEM-SS | + | Propyl Urea | No Virus | 0 | 0 | 0 | 0 | 0 |
| | | | + HIV | 14 | 16 | 12 | 9 | 10 |
| CEM-SS | + | Butyl Urea | No Virus | 0 | 0 | 0 | 0 | 0 |
| | | | + HIV | 4 | 7 | 5 | 2 | 2 |

The present invention is not to be limited to the preferred embodiments described above, but is only to be limited by the scope of the following claims.

What is claimed is:

1. A method for treating viral infections in a warm-blooded animal having a viral infection which comprises administering to said warm-blooded animal an antivirally effective amount of a monosubstituted lower alkyl urea.

2. The method of claim 1, wherein the virus is the HIV virus.

3. The method of claim 1, wherein the virus is the hepatitis virus.

4. The method of claim 1, wherein the virus is selected from the group consisting of Herpes I virus, Herpes II virus, and AIDS virus.

5. The method of claim 1, wherein the alkyl urea has the formula $$R—NH—CO—NH_2$$

wherein R is lower alkyl having from 1 to 8 carbon atoms.

6. The method of claim 1, Wherein R is lower alkyl having from 1 to 6 carbon atoms.

7. The method of claim 1, wherein R is lower alkyl having from 1 to 4 carbon atoms.

8. The method of claim 1, wherein the monosubstituted lower alkyl urea is administered orally.

9. The method of claim 1, wherein the monosubstituted lower alkyl urea is administered intravenously or by injection.

10. The method of claim 1, wherein the monosubstituted alkyl urea is administered extracorporealy.

11. The method of claim 1, wherein the monosubstituted lower alkyl urea is added to blood or it components, in vivo or in vitro, followed by the incubation and/or transfusion.

12. The method of claim 1, wherein the monosubstituted lower alkyl urea is administered topically.

13. The method of claim 1, wherein the monosubstituted lower alkyl urea is administered by a transdermal patch.

14. The method of claim 1, wherein the virus is alive.

15. A method for treating viral infection in a medium selected from the group consisting of blood supply, blood bank, hospital blood supply, surfaces of all kinds, or mixtures thereof being virally infected which comprises administering to said medium an antivirally effective amount of a monosubstituted lower alkyl urea.

* * * * *